US008049143B2

(12) United States Patent
Andel et al.

(10) Patent No.: US 8,049,143 B2
(45) Date of Patent: Nov. 1, 2011

(54) HOT PLATE HEATER FOR A RESPIRATORY SYSTEM

(75) Inventors: David F. Andel, Lawrenceville, GA (US); Keith J. Bradley, Atlanta, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1037 days.

(21) Appl. No.: 11/926,982

(22) Filed: Oct. 29, 2007

(65) Prior Publication Data
US 2009/0107980 A1 Apr. 30, 2009

(51) Int. Cl.
H05B 3/68 (2006.01)
H05B 3/60 (2006.01)
A61M 15/00 (2006.01)

(52) U.S. Cl. .................. 219/443.1; 392/324; 128/203.12

(58) Field of Classification Search .... 219/443.1–468.2, 219/429, 433, 436, 437, 438, 538, 546; 392/322, 392/324, 386; 128/203.12–203.17
See application file for complete search history.

(56) References Cited

U.S. PATENT DOCUMENTS

| 3,028,476 | A | * | 4/1962 | Hug .............................. 219/443.1 |
| 3,659,604 | A | * | 5/1972 | Melville et al. .......... 128/203.27 |
| 3,697,728 | A | | 10/1972 | Stirzenbecher |
| 3,806,102 | A | | 4/1974 | Valenta et al. |
| 3,982,095 | A | * | 9/1976 | Robinson ....................... 392/403 |
| 4,095,086 | A | | 6/1978 | Ohnmacht et al. |
| 4,203,027 | A | | 5/1980 | O'Hare et al. |
| 4,215,267 | A | * | 7/1980 | Kaebitzsch .................... 219/439 |
| 4,225,542 | A | | 9/1980 | Wall et al. |
| 4,291,838 | A | | 9/1981 | Williams |
| 4,447,711 | A | | 5/1984 | Fischer |
| 4,613,745 | A | | 9/1986 | Marotta et al. |
| 4,652,408 | A | | 3/1987 | Montgomery |
| 4,676,237 | A | | 6/1987 | Wood et al. |
| 4,715,269 | A | | 12/1987 | Stoner |
| 4,772,777 | A | | 9/1988 | Weller et al. |
| 4,888,465 | A | | 12/1989 | Hoffmann |
| 5,031,612 | A | | 7/1991 | Clementi |
| 5,345,063 | A | * | 9/1994 | Reusche et al. ............... 219/441 |
| 5,529,060 | A | | 6/1996 | Salmon et al. |
| 5,704,799 | A | * | 1/1998 | Wood ............................ 439/281 |
| 5,844,206 | A | * | 12/1998 | Steiner et al. ............ 219/452.12 |
| 5,943,473 | A | | 8/1999 | Levine |

(Continued)

FOREIGN PATENT DOCUMENTS
WO 2008/056993 A2 5/2008
(Continued)

OTHER PUBLICATIONS

Manual for Fisher & Paykel Model Nos. MR700, MR720, MR730 Respiratory Humidifiers (Mar. 1998) (48 pages).

(Continued)

Primary Examiner — Sang Paik
(74) Attorney, Agent, or Firm — Wood, Herron & Evans, LLP

(57) ABSTRACT

A heater unit for a respiratory system includes a hot plate heater including a heat conducting hot plate and a plastic hub mounted together. The hot plate may define a thin heat conducting disc and may further define a depending flange circumferentially surrounding the hub. The hub and flange may include snap-together apertures and fingers. The hub is mounted to a housing of the heater unit.

29 Claims, 7 Drawing Sheets

U.S. PATENT DOCUMENTS

| | | | |
|---|---|---|---|
| 5,981,914 A * | 11/1999 | Schultheis | 219/452.11 |
| 6,037,572 A | 3/2000 | Coates et al. | |
| 6,102,037 A | 8/2000 | Koch | |
| 6,150,636 A | 11/2000 | Bogdanski et al. | |
| 6,367,472 B1 | 4/2002 | Koch | |
| 6,394,084 B1 | 5/2002 | Nitta | |
| 6,414,271 B2 | 7/2002 | Yokoyama et al. | |
| 6,584,974 B1 | 7/2003 | Ratner | |
| 6,753,508 B2 | 6/2004 | Shirakawa | |
| 6,772,999 B2 | 8/2004 | Lipscombe et al. | |
| 6,805,119 B2 | 10/2004 | Hoffmann et al. | |
| 6,831,256 B2 | 12/2004 | Haasis et al. | |
| 6,875,957 B2 | 4/2005 | Taplan et al. | |
| 6,897,411 B2 | 5/2005 | Beer et al. | |
| 6,921,882 B2 | 7/2005 | Gadow et al. | |
| 6,924,468 B2 | 8/2005 | Abbott et al. | |
| 6,976,489 B2 | 12/2005 | Mantell et al. | |
| 6,988,497 B2 | 1/2006 | Levine | |
| 7,478,635 B2 | 1/2009 | Wixey et al. | |
| 2003/0066526 A1 | 4/2003 | Thudor et al. | |
| 2004/0221843 A1 | 11/2004 | Baecke | |
| 2004/0245239 A1 | 12/2004 | McWilliams | |
| 2005/0067400 A1 | 3/2005 | Hoh | |
| 2005/0089319 A1 | 4/2005 | Mitsunaga et al. | |
| 2007/0051368 A1 | 3/2007 | Seakins | |

FOREIGN PATENT DOCUMENTS

| | | |
|---|---|---|
| WO | 2010140903 A1 | 12/2010 |

OTHER PUBLICATIONS

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Operating Manual for Fisher & Paykel Model Nos. MR700, MR720, MR730 Respiratory Humidifiers (Mar. 1994) (46 pages).

Cardinal Health RT110 Data for Circuits, reprinted from the internet Jun. 3, 2006 (2 pages).

Fisher & Paykel Airway Temperature Probes Instructions for Use (3 pages) (2003).

* cited by examiner

HOT PLATE HEATER FOR A RESPIRATORY SYSTEM

FIELD OF THE INVENTION

The present invention relates to a hot plate heater for a respiratory system and, more particularly, a hot plate heater for the heater unit of the humidifier system of such a respiratory system.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit. An expiratory limb hose or conduit may be provided to carry expelled air and other gas(es) from the patient back to the ventilator or to atmosphere.

It is typically desired to warm and impart humidity to the breathable gas before it is provided to the patient. For that purpose, many respiratory systems include a humidification system including a heater unit and a disposable water chamber adapted to be heated by the heater unit. The heater unit supports a hot plate heater, which may be comprised of one or more heating elements and a metal plate defining a hot plate. The heater unit also typically houses the necessary electrical and electronic components to regulate the temperature of the heater as well as heating circuits of the inspiratory and/or expiratory limbs of the breathing circuit. A wall of the chamber, such as the bottom surface thereof, is thermally conductive. The chamber is removably supported on the heater unit with the bottom surface in thermal contact with the hot plate of the heater to thus heat the water in the chamber. The chamber may be manually refillable, or there may be a water source to selectively fill the chamber as it empties. The breathable gas is coupled to the chamber, and is passed through the chamber to be heated and humidified. The inspiratory limb carries the heated and humidified gas to the patient. Examples of heater units, chambers and vented water supplies are shown in U.S. Pat. Nos. 6,988,497 and 5,943,473; and co-pending U.S. patent application Ser. No. 11/469,086 filed Aug. 31, 2006 and Ser. No. 11/469,113 filed Aug. 31, 2006.

The hot plate is typically a thick machined or cast metal member so as to have a significant thermal mass. Such thick metal members can be costly and can be undesirable for other reasons. Moreover, the hot plate heater is typically mounted to the heater unit by fastening mount members, such as spring loaded metal screws connected to an underlying support structure of the heater unit. Assembly of such hot plate heaters to the heater unit can be time-consuming and costly. Moreover, the mount members can conduct heat away from the hot plate thereby undesirably reducing thermal efficiency. In some situations, the underside or lower edge of the hot plate may be undesirably exposed to air further reducing thermal efficiency such as due to convection losses.

SUMMARY OF THE INVENTION

The present invention provides a hot plate heater which is less costly, more thermally efficient, and easier to assemble than conventional hot plate heaters. To that end, and in accordance with the principles of the present invention, the hot plate heater includes a hot plate defined by a thin heat conducting disc and a thermoplastic hub to which the disc is mounted, with the hub being coupled to the heater unit. One or more heating elements are disposed between the disc and the hub to heat the hot plate with the hub serving as a thermal break to limit convection losses from the underside of the disc thus enhancing thermal efficiency. Further, by coupling the hot plate to the heater unit via the thermoplastic hub, heat transfer out of the disc other than into the chamber is reduced thus further enhancing thermal efficiency and also simplifying assembly. The thin heat conducting disc has low thermal mass and so can respond quickly to heat up or cool down as desired, thereby providing enhanced ability to regulate the temperature thereof as well as further enhancing thermal efficiency. The thin heat conducting disc can be efficiently manufactured at low cost such as by being stamped and/or drawn from sheet metal stock.

The hot plate and hub may be adapted to snap together to further simplify assembly. In that regard, the hot plate may include a flange depending from the peripheral edge of the thin heat conducting disc to define a lower edge of the hot plate. The flange is in surrounding relationship to the hub. The flange and hub may include cooperating apertures and cantilevered mount fingers which engage together when the hot plate and hub are mounted together. The mount fingers may include tabs that snap into the apertures for quick and easy mounting of the hot plate to the hub. The hub also serves as a thermal break adjacent the flange to minimize convection losses from the lower edge of the hot plate.

By virtue of the foregoing, there is thus provided a hot plate heater which is less costly, more thermally efficient, and easier to assemble than conventional hot plate heaters. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
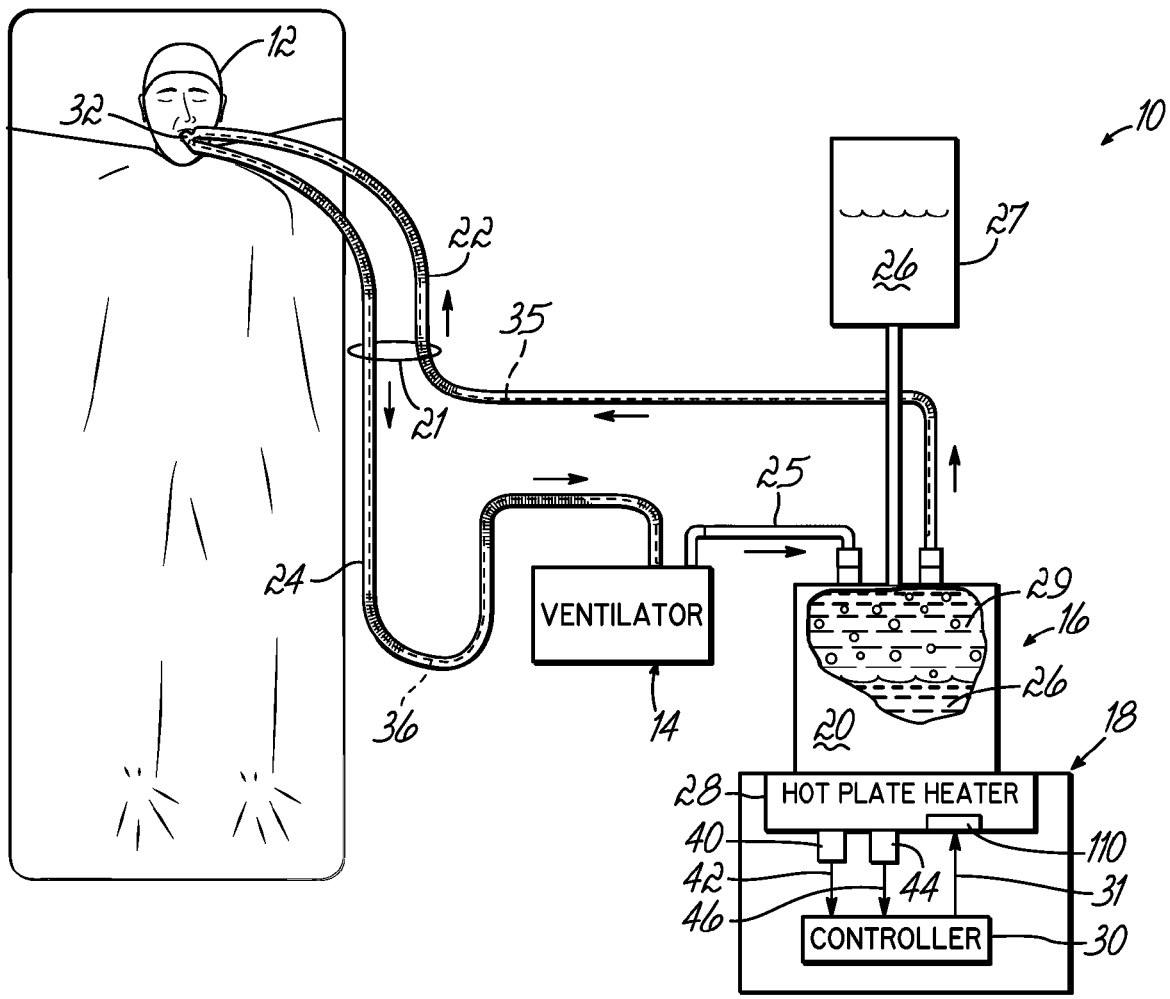
FIG. 1 is a schematic representation of a respiratory system with a humidification system including a heater unit having a hot plate heater constructed in accordance with the principles of the present invention.
Figure 2:
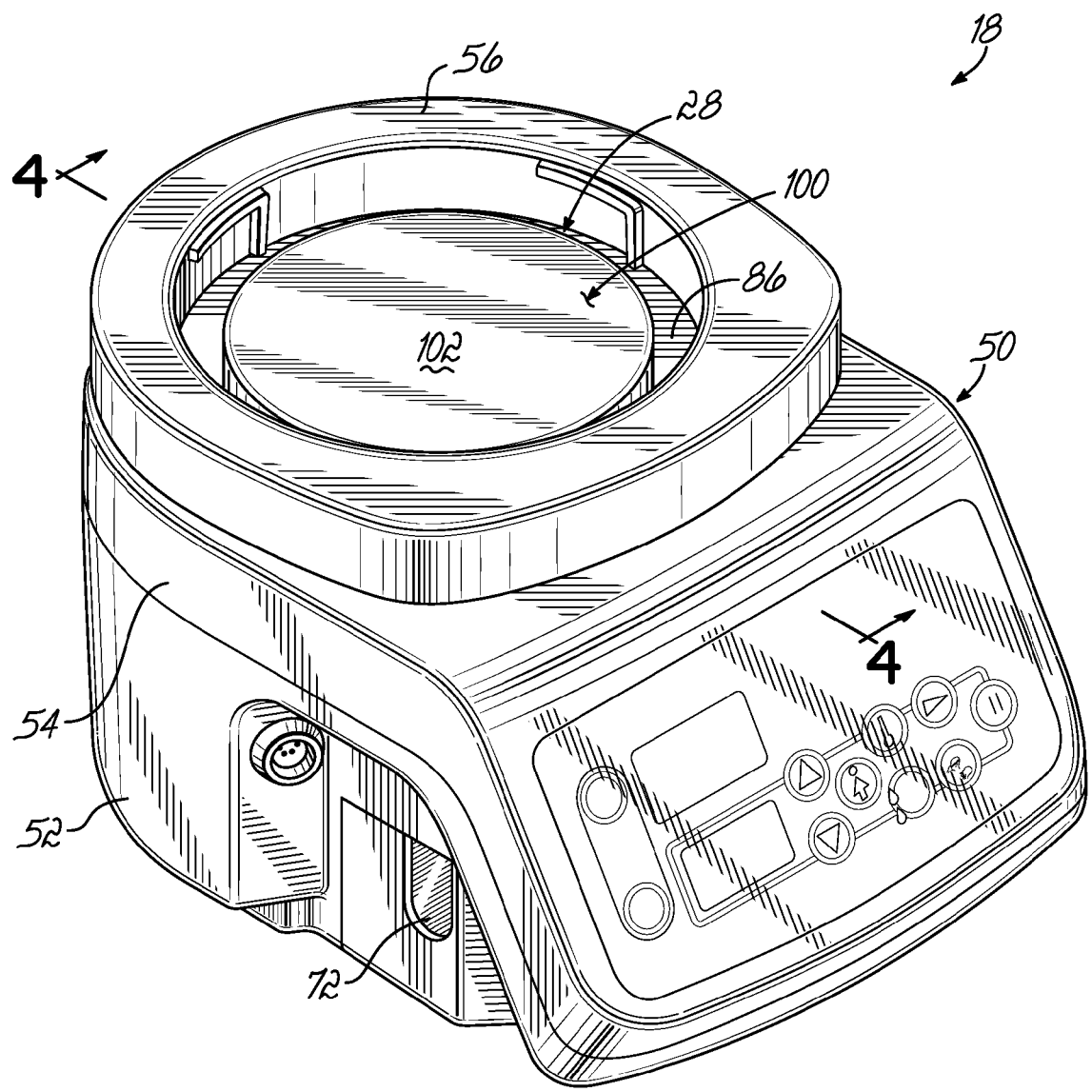
FIG. 2 is a perspective view of the heater unit of FIG. 1.

FIG. 1 is an exemplary respiratory system 10 for supplying breathable gases to a patient 12. In the illustrated embodiment, the respiratory system 10 includes a ventilator 14, and a humidification system 16 including a heater unit 18, a heatable container for water such as a disposable chamber 20, and a breathing circuit 21 having a first elongated hose or conduit 22 defining an inspiratory limb and second elongated hose or conduit 24 defining an expiratory limb. Ventilator 14 drives breathable gas, such as oxygen, anesthetic gas and/or air, through gas conduit 25 and into an inlet of chamber 20. Water 26 is received in chamber 20, either by being poured in manually or automatically from a water supply 27 such as a bag or bottle, which may be vented. Chamber 20 is heated by a hot plate heater 28 of heater unit 18 with the temperature of hot plate heater 28 being regulated by controller 30 of heater unit 18 as at 31. Heated water vapor 29 may also be produced within chamber 20 above the level of water 26 therein.

The gas from conduit 25 passes over or through heated water 26 and/or through heated water vapor 29 to become heated and humidified. The heated and humidified gas flows from chamber 20 through inspiratory limb 22 to a breathing attachment 32. Breathing attachment 32 may be coupled to an invasive apparatus such as an orotrachael tube, or a non-invasive apparatus such as a mask. to facilitate delivery of the gas passed through inspiratory limb 22 to patient 12. Expiratory limb 24 allows exhaled air and other gas(es) expelled from patient 12 to pass back to ventilator 14, the atmosphere or elsewhere. Inspiratory limb 22 and/or expiratory limb 24 may be heated by respective heating circuits 35, 36 responsive to controller 30 via control lines (not shown). Temperature measurements may be taken of the heated and humidified gas exiting chamber 20 and/or at breathing attachment 32 with probes (not shown) which communicate the measurements to controller 30 via one or more patient temperature cables (also not shown). Examples of probes and patient temperature cables which may be used in respiratory system 10 are shown in concurrently-filed U.S. patent application Ser. No. 11/927,020, and concurrently-filed U.S. patent application Ser. No. 11/927,077, the disclosures of both of which are incorporated herein by reference in their entireties.

A temperature sensitive device 40 such as a themistor may be thermally coupled to hot plate heater 28. The temperature of hot plate heater 28 may be provided to controller 30 as at 42 based on temperature readings from thermistor 40. Also, a fuse or other thermal cutoff device 44 may be thermally coupled to hot plate heater 28 to provide a cutoff signal as at 46 to controller 30 in the event hot plate heater 28 overheats. Temperature measurements from hot plate heater 28 and/or from the probes (not shown) are utilized by controller 30 to regulate the temperature of hot plate heater 28 and/or heating circuits 35, 36. Various details of a controller 30 and associated electric and electronics are provided in the following concurrently-filed U.S. patent applications, the disclosures of which are incorporated herein by reference in their entireties: U.S. patent application Ser. No. 11/926,990, U.S. patent application Ser. No. 11/927,000, U.S. patent application Ser. No. 11/927,004; U.S. patent application Ser. No. 11/927,013; U.S. patent application Ser. No. 11/927,054; and U.S. patent application Ser. No. 11/927,068.

Figure 3:
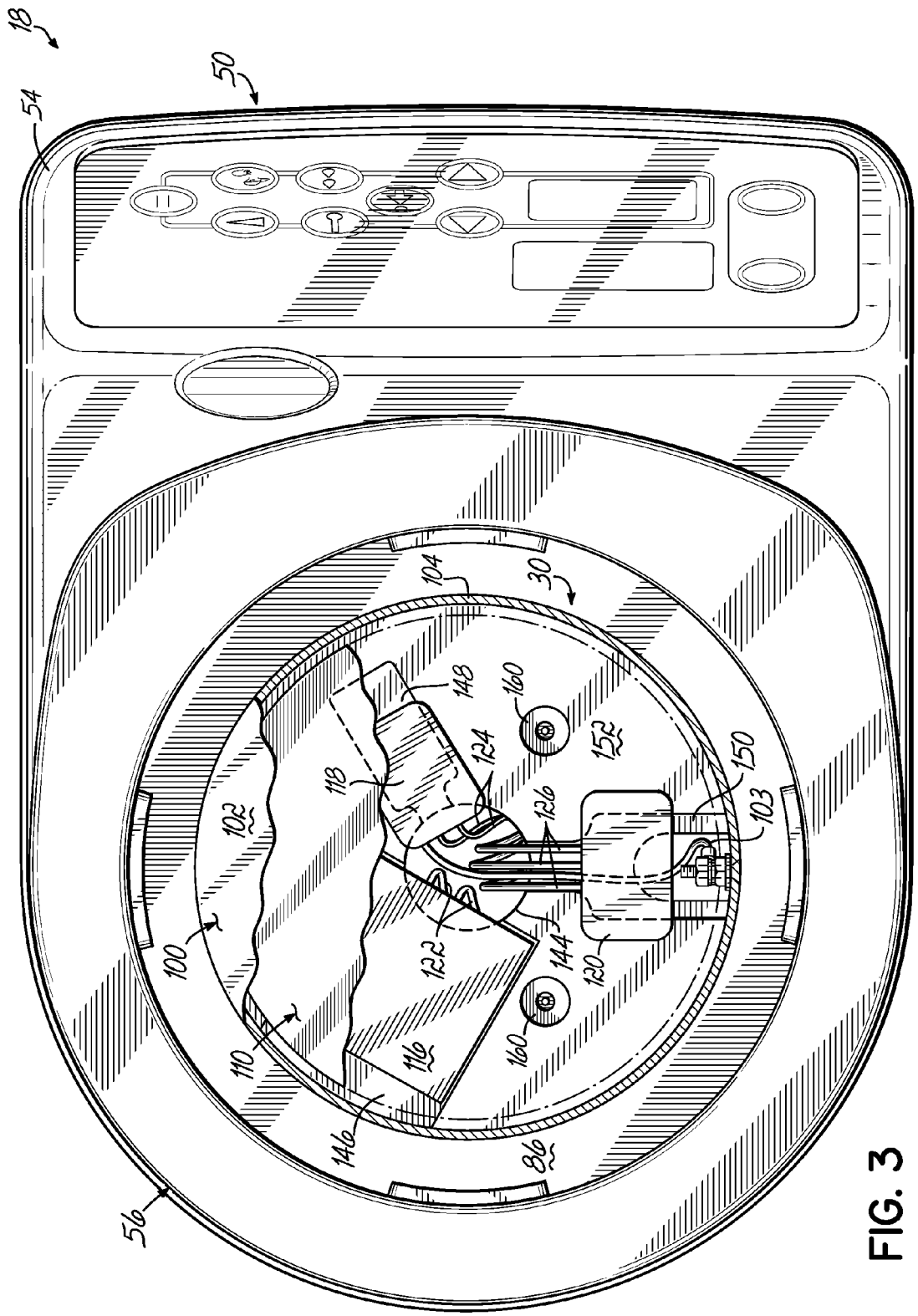
FIG. 3 is a top plan, partially cut away view of the heater unit of FIG. 2.
Figure 4:
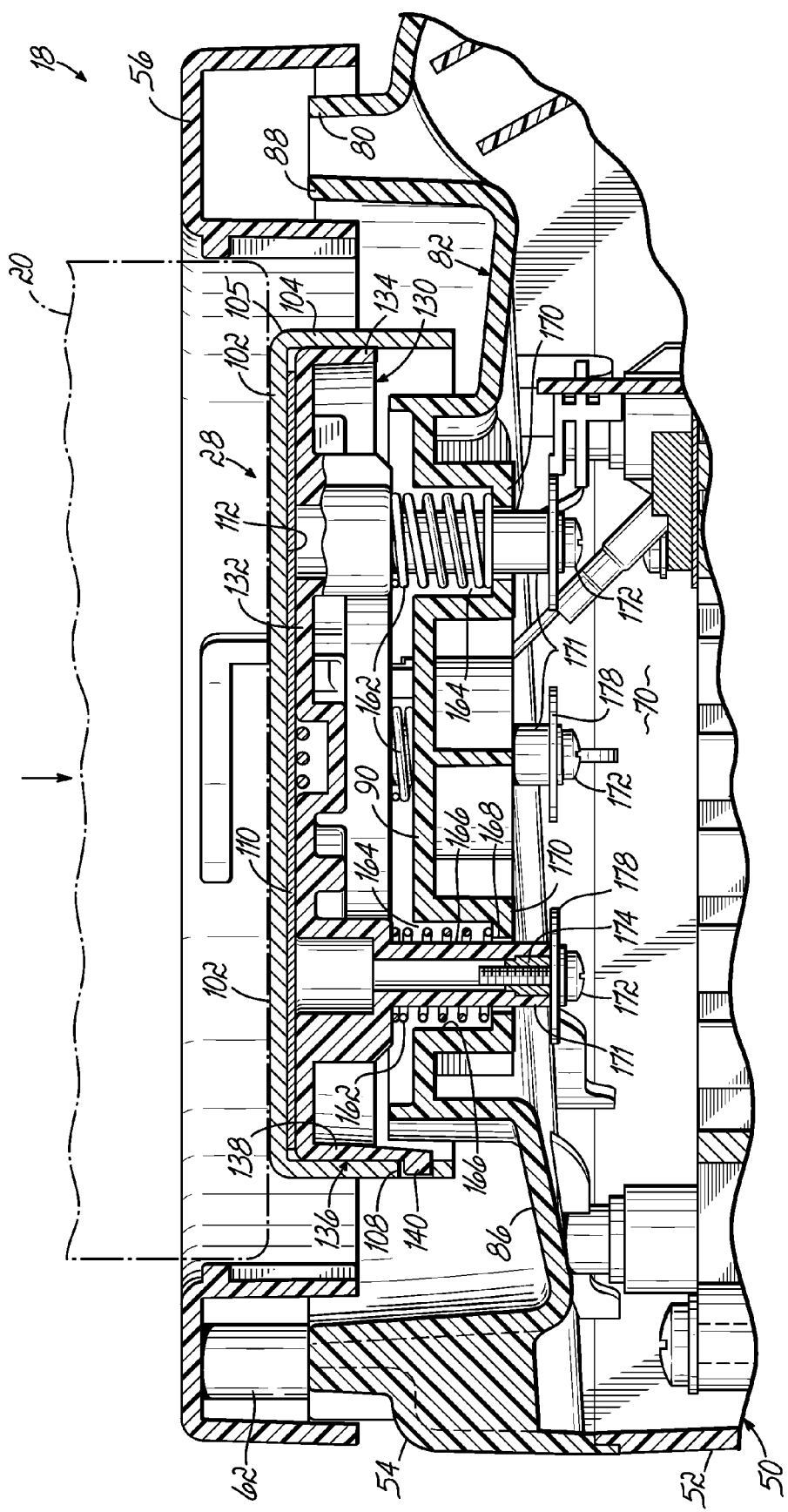
FIG. 4 is a cross-sectional view taken along line 4-4 in FIG. 2.

Referring further to FIGS. 2 through 7, heater unit 18 includes a housing 50 having a lower housing 52 and an upper housing 54 to which is mounted hot plate heater 28. Heater unit 18 includes a locking ring 56 secured to upper housing 54 in surrounding relationship to hot plate heater 28 such as with a plurality of bolts 58 passing upwardly through bosses 60 formed in the upper housing 54 (FIG. 5) and into corresponding ones of a plurality of bosses 62 (one shown in FIG. 4) formed in locking ring 56. Locking ring 56 is configured to removably receive a lower portion of chamber 20 in thermal communication with hot plate heater 28 (as exemplified in dashed line in FIG. 4). Lower housing 52 and upper housing 54 combine to define an interior chamber 70 (FIG. 4). Heater unit 18 may also include a junction box 72 for coupling to a source of AC power for powering the electric and electronic components within housing 50, including controller 30 and various significant heat generating components such as a transformer and power switches (not shown) which may form part of or be associated with controller 30. Housing 50 and the components therein may be arranged to advantageously remove heat from interior chamber 70 as described in concurrently-filed U.S. patent application Ser. No. 11/927,038 the disclosure of which is incorporated herein by reference.

Figure 5:
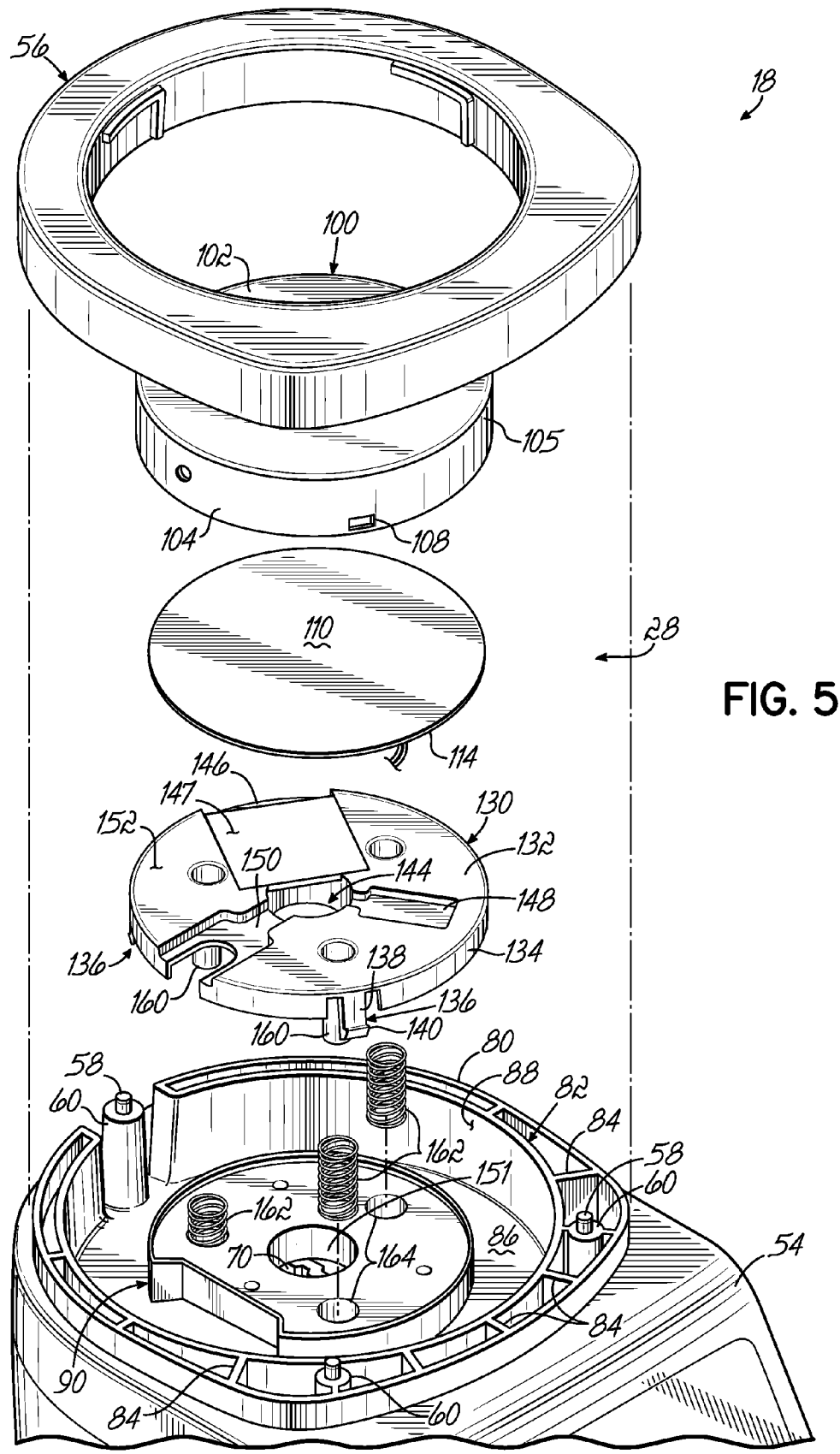
FIG. 5 is a partial, exploded perspective view of the heater unit of FIG. 2.
Figure 6:
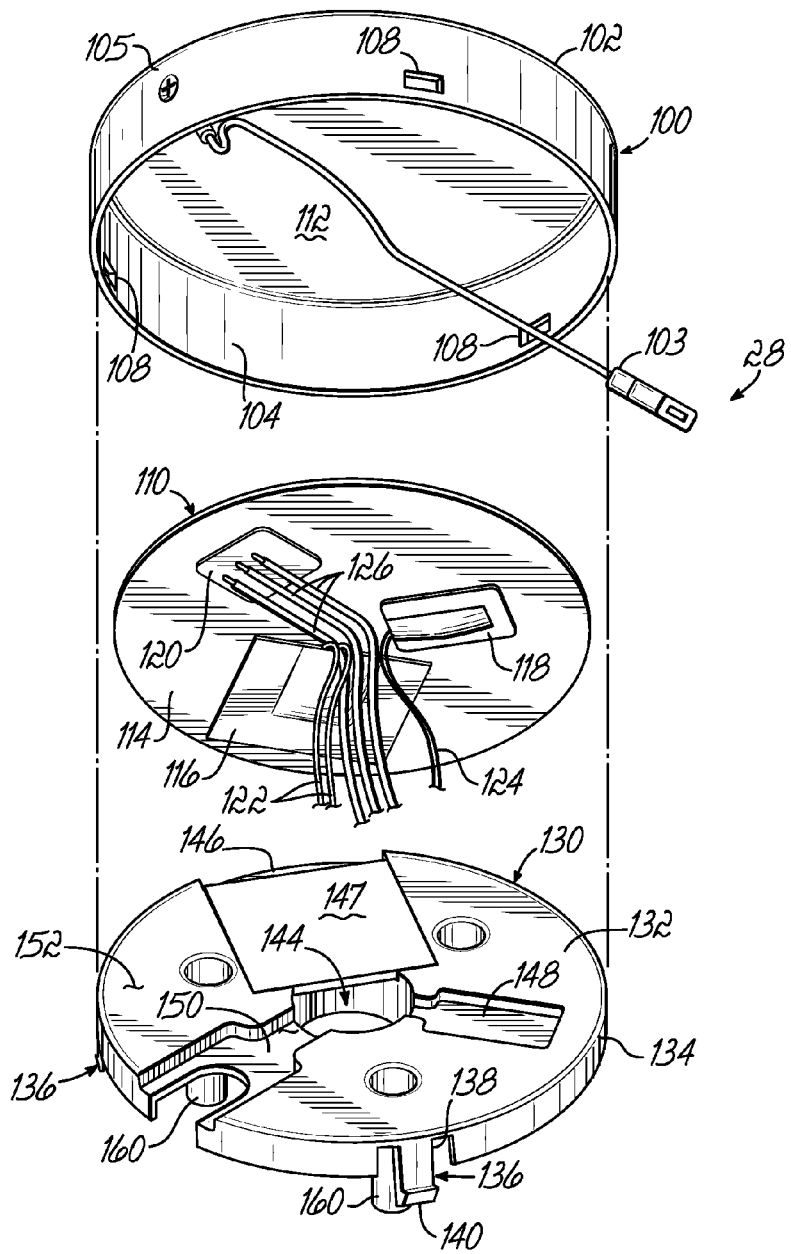
FIG. 6 is an exploded perspective view of the hot plate heater of the heater unit of FIG. 1.

Upper housing 54 of housing 50 may include an upper flange 80 extending about a perimeter of upper housing 54. Upper housing 54 may also include a support structure, indicated generally at 82, interconnected with flange 80 by a plurality of circumferentially spaced connecting struts 84, having varying lengths, as shown in FIG. 5. Support structure 82 includes a base 86 and a flange 88 extending upwardly from the base 86 and substantially around the perimeter of support structure 82. Flanges 80 and 88 extend into locking ring 56. Support structure 82 includes a platform 90 extending upwardly from the base 86 for supporting hot plate heater 28.

Figure 7:
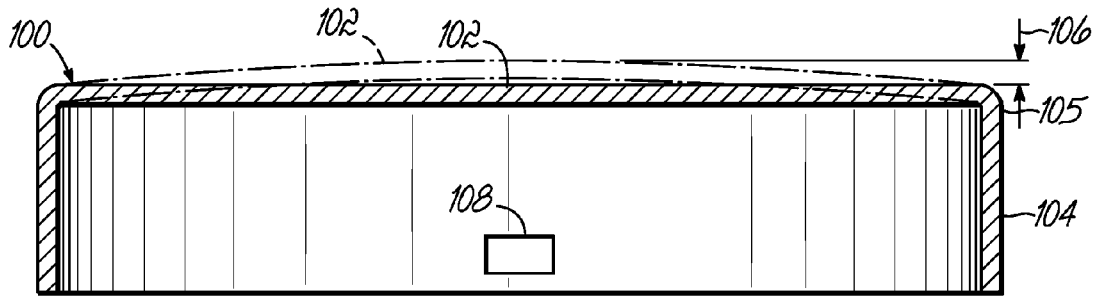
FIG. 7 is a cross-sectional view of the hot plate of the hot plate heater of FIG. 6.

Hot plate heater 28 includes a hot plate 100 which, in the embodiment shown, is defined by a thin heat conducting disc 102 (FIG. 7). Hot plate 100 may be of metal and may include a ground wire 103 (FIG. 5) secured thereto. Hot plate 100 may also include a flange 104 depending from the peripheral edge 105 of disc 102 and, if of metal, may provide the connection to ground wire 103. In the illustrated embodiment, disc 102 is round and flange 104 is an annular flange. Flange 104 may include a plurality of spaced apertures 108 (shown particularly in FIG. 6) formed therein for reasons explained below. In one embodiment, hot plate 100 is made of metal, such as aluminum coated with nickel, in a one piece construction and stamped and drawn from sheet metal stock to thus create hot plate 100 in a cost effective process.

Disc 102 may define a top surface of hot plate 100 which is substantially flat or it may have a slight convex shape, as shown in an exaggerated view in FIG. 7. Advantageously, the convex shape provides a displacement from a horizontal plane to enhance contacting engagement between disc 102 and a heat conducting bottom surface (not shown) of chamber 20 to facilitate thermal communication therebetween. The maximum displacement from a horizontal plane is advantageously about 0.006 inch. Disc 102 is relatively thin, such as about 0.060 inch thick, and accordingly has low thermal mass so as to quickly heat up as desired and/or cool off as desired to thus be very thermally efficient.

A heating element 110 is in thermal communication with hot plate 100 such as by being secured to the underside surface 112 of disc 102. Signals from controller 30 as at 31 (FIG. 1) selectively energize heating element 110 to heat up disc 102. Heating element 110 may include one or more circuits of resistive wires, such as etched copper foil heating elements, disposed between two relatively thin layers of an elastomeric material such as silicone (not shown). Heating element 110 can be bonded to underside surface 112 by conventional processes, such as a vulcanization process. Patches 116, 118 and 120 are bonded to surface 112 (FIG. 6) to provide electrical junctions and strain relief for wires 122, 124 and 126, respectively. By way of example, wires 122 may carry power signals 31 to heating element 110 (such as the resistive wires thereof) to regulate the temperature of disc 102 as determined by controller 30. Wires 124 may carry temperature readings 42 from thermistor 40 to controller 30, and wires 126 may carry cutoff signals 46 from cutoff device 44 to controller 30. Wires 122, 124 and 126 can be routed to interior 70 of housing 50 in a manner that enhances the service life of the wires, and associated electrical junctions (not shown) as will be explained below.

Hot plate heater 28 further includes a hub 130 (FIGS. 4 through 6) having a support platform 132 and a flange 134 integral with platform 132 and extending downwardly from platform 132. Hub 130 includes a plurality of cantilevered mount fingers 136 (one shown in FIG. 5). Each finger 136 has a proximal end 138 integral with flange 134 and a distal end 140 defining a tab. Each tab 140 engages one of the apertures 108 formed in flange 104 of hot plate 100 in a snap fit in order to easily mount hot plate 100 to hub 130.

Hub 130 includes a generally centrally disposed aperture 144 formed therein that extends through platform 132. Aperture 144 communicates with interior chamber 70 of housing 50. Platform 132 also includes recesses 146, 148 and 150 formed therein. Each of recesses 146, 148 and 150 extends through an upper surface 152 of platform 132 and can be configured to receive respective ones of patches 116, 118, 120. For example, in the illustrated embodiment, recess 146 is configured to receive patch 116 and associated wires 122, with patch 116 and the portion of wires 122 secured to heating member 110 by patch 116 disposed within recess 146. A pad or cushion 147, that can be made of an elastomeric material, may be disposed within recess 146 (FIGS. 5 and 6), to provide additional strain relief for wires 122.

As shown in FIG. 3, patches 118 and 120 need not be disposed entirely within recesses 148 and 150, respectively, (a lower portion of patch 118 is disposed within recess 148). However, the portion of wires 124 and 126 coupled through patches 118 and 120, respectively, are disposed within recesses 148 and 150, respectively. Recesses 146, 148 and 150 combine with aperture 144 and an aperture 151 (FIG. 5) formed in platform 90 of support structure 82 of upper housing to permit wires 122, 124 and 126 to be routed from hot plate 100 to interior chamber 70 of housing 50 for electrical coupling with controller 30 in a strain-relieved manner that enhances the service life of wires 122, 124 and 126.

Hot plate 100 is mounted on hub 130 by first aligning apertures 108 in flange 104 with tabs 140 of hub 130, which causes recesses 146, 148 and 150 of hub platform 132 to be aligned with patches 116, 118 and 120, respectively. Hub 130 is then inserted against or into hot plate member 100 such that flange 104 of hot plate 100 is concentrically disposed relative to flange 134 of hub 130 and tabs 140 snap into engagement with apertures 108. In this assembled condition, patches 116, 118 and 120 are disposed within recesses 146, 148 and 150 and heating element 110 is disposed between disc 102 and hub 130.

Hub 130 is advantageously made of a thermoplastic material and provides thermal and electrical insulation for hot plate heater 28. The thermoplastic material of hub 130 creates a thermal break against conduction heat transfer losses from hot plate 100 to housing 50 of heater unit 18. With heating element 110 disposed between hot plate 100 and hub 130, there is reduced convection cooling of hot plate 100 as compared to prior systems where the lower side of the hot plate is exposed to airflow. Examples of suitable thermoplastic materials include Ultem® and polyphenyl sulfone. The thermoplastic material of hub 130 also acts as an electrical insulator such that occurrence of electrical short circuits within heating element 110 and/or wires 122, 124, 126 routed and extending from hot plate 100 is reduced relative to prior systems lacking such electrical insulation.

Hot plate heater 28 may be mounted to housing 50 via hub 130 to reduce heat transfer from hot plate 100 into housing 50. To that end, hub 130 includes a plurality of spaced posts 160 integral with platform 132 and extending downwardly from platform 132. Hot plate heater 28 further includes a plurality of resilient members 162, which can comprise coil springs, with each of the posts 160 extending through one of the resilient members 162. Platform 90 of the support structure 82 includes a plurality of receptacles 164 extending therethrough and each having a relatively larger upper opening 166, which can be a hole having a relatively larger diameter, and a relatively smaller lower opening 168, which can be a hole having a relatively smaller diameter, that communicates with opening 166. Each opening 166 combines with the corresponding opening 168 to define a shelf 170 of support structure 82. Each post 160 and corresponding resilient member 162 is inserted into one of the receptacles 164 so that post 160 extends through both openings 166 and 168 with a distal end 171 of posts 160 extending below the corresponding shelf 170. Each resilient member 162 is captured between the corresponding shelf 170 and platform 132 of hub 130. Posts 160 are free to move within receptacles 164 relative to housing 50 in response to the weight of chamber 20 (and the water 26 therein) and/or forces applied to chamber 20 such as during mounting thereof to heater unit 18

Each post 160 can be prevented from disengaging the corresponding receptacle 164 by threading a fastener 172, such as a bolt, into a threaded insert 174 inserted into the hollow distal end 171 of post 160 to capture a washer 178, which is larger than opening 168 of receptacle 164, between the distal end 171 of post 160 and the head of fastener 172. The force that resilient members 162 exert on hub 130 varies with the application. In one embodiment, the total force exerted by members 162 ranges from about 5 lbs. to about 9 lbs.

Figure 8:
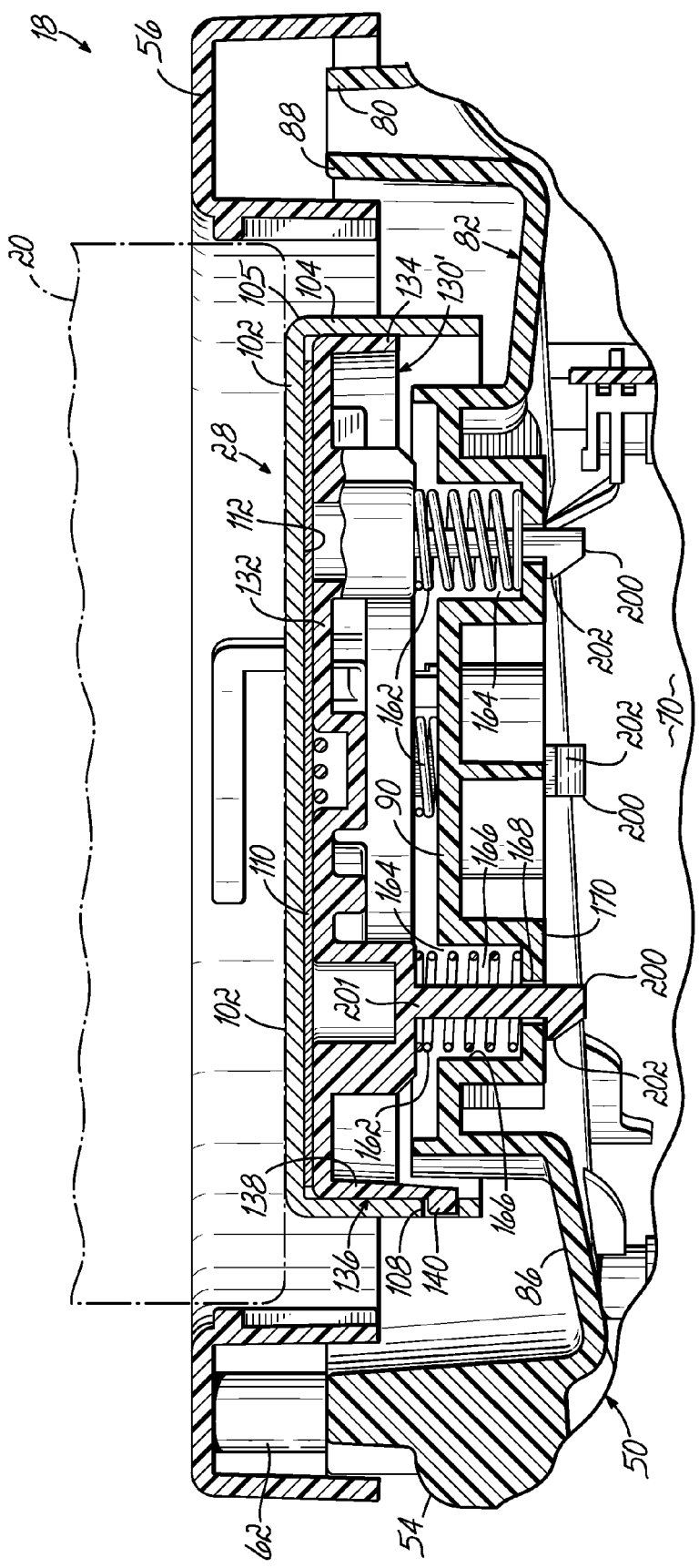
FIG. 8 is a view similar to FIG. 3 showing an alternative hub for the hot plate heater.

FIG. 8 illustrates an alternative hub 130' for mounting hot plate 100 to housing 50. Hub 130' is substantially similar to hub 130 (and so the same reference numbers are used for like structure) except that posts 160 are replaced with posts 200 that extend downwardly from hub 130'. Posts 200 each include a proximal end 201 integral with the platform 132 of hub 130' and a distal end 202 defining a tab. Each of posts 200 extends through one of the resilient members 162 and extends into and through a corresponding one of the receptacles 164 such that tab 202 thereof is disposed below the corresponding one of shelves 170. Each tab 202 is deformable so it can be pushed through the lower opening 168 of the corresponding receptacle 164.

In use, heater unit 18 is put into service as part of respiratory system 10 with chamber 20 and breathing circuit 21. Heater unit 18 can be removably secured to a structure by a lockable mounting mechanism (not shown) removably secured to the lower housing 52 of heater unit 18. Additional details of a lockable mounting mechanism are provided in concurrently-filed U.S. patent application Ser. No. 11/927,044 the disclosure of which is incorporate herein by reference in its entirety. With hub 130 (or 130') acting as a thermal break, convection losses from the underside 112 of disc 102 are minimized to thus enhance thermal efficiency of hot plate heater 28. Further, heat transfer out of hot plate heater 28 other than into chamber 20 is reduced, and assembly is simplified, by coupling hot plate heater 28 to housing 50 via plastic hub 130 (or 130'). Use of thin disc 102 also provides a low thermal mass (and low physical mass) to thus provide a thermally efficient hot plate heater 28, but which can be efficiently manufactured at low cost.

By virtue of the foregoing, there is thus provided a hot plate heater which is less costly, more thermally efficient, and easier to assemble than conventional hot plate heaters.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. To that end, while hot plate 100 is described as being metal and being round, other heat conducting materials or shapes may be utilized. Also, various heating elements may be used as desired. Moreover, the hot plate and heating element may be combined such that the heating element is still considered in thermal communication with the hot plate. The invention in its broader aspects is, therefore, not limited to the specific details, representative apparatus and method, and illustrative examples shown and described. Accordingly, departures may be made from such details without departing from the spirit and scope of the general inventive concept.

Having described the invention, what is claimed is:

1. A hot plate heater comprising:
   a metal hot plate consisting essentially of a thin disc and an annular flange depending from a peripheral edge of the thin disc, the thin disc having a lower disc surface;
   a plastic hub adapted to be mounted to a heater unit, the hub having an upper platform and a flange extending from the upper platform, the hot plate being mounted with the flanges secured together such that the upper platform of the hub is aimed at the thin disc and the annular flange of the hot plate is about the flange of the hub; and
   a heating element disposed intermediate the lower surface of the thin disc of the hot plate and the upper platform of the hub, the heating element being thermally coupled to the hot plate.

2. The hot plate heater of claim 1, the heating element being sandwiched between the lower disc surface of the thin disc of the hot plate and the upper platform of the hub.

3. The hot plate heater of claim 1, the annular flange of the hot plate being circumferentially disposed about the hub.

4. The hot plate heater of claim 1, the thin disc and the annular flange of the hot plate being of one-piece construction.

5. The hot plate heater of claim 1, the annular flange of the hot plate including a plurality of spaced apertures, the hub including a plurality of spaced, cantilevered mount fingers, the apertures and mount fingers cooperating to secure the hot plate and the hub.

6. The hot plate heater of claim 5, each of the mount fingers including a tab adapted to snap into a respective aperture.

7. The hot plate heater of claim 1, the hot plate being of nickel-plated aluminum.

8. The hot plate heater of claim 1, the hub being of polyphenyl sulfone.

9. The hot plate heater of claim 1, the thin disc of the hot plate being slightly convex.

10. The hot plate heater of claim 1, the hub including a plurality of spaced posts adapted to couple to a support of a heater unit.

11. The hot plate heater of claim 10, the posts each adapted to receive threaded inserts.

12. The hot plate heater of claim 10, each post defining a tab adapted to snap into a respective receptacle of a heater unit.

13. The hot plate heater of claim 10 further comprising a plurality of springs associated with the plurality of posts.

14. A heater unit comprising:
    a housing;
    a hot plate heater including:
       a metal hot plate consisting essentially of a thin disc and an annular flange depending from a peripheral edge of the thin disc, the thin disc having a lower disc surface;
       a plastic hub having an upper platform and a flange extending from the upper platform, the hot plate being mounted on the plastic hub with the flanges secured together such that the upper platform of the hub is aimed at the thin disc and the annular flange of the hot plate is about the flange of the hub; and
       a heating element disposed intermediate the lower surface of the thin disc of the hot plate and the upper platform of the hub, the heating element being thermally coupled to the hot plate;
    hub the plastic hub being mounted to the housing whereby to mount the hot plate heater to the housing.

15. The heater unit of claim 14, the heating element being sandwiched between the lower disc surface of the thin disc of the hot plate and the upper platform of the hub.

16. The heater unit of claim 14, the annular flange of the hot plate being circumferentially disposed about the hub.

17. The heater unit of claim 14, the disc and the annular flange of the hot plate being of one-piece construction.

18. The heater unit of claim 14, the annular flange of the hot plate including a plurality of spaced apertures, the hub including a plurality of spaced, cantilevered mount fingers, the apertures and mount fingers cooperating to secure engage the hot plate and the hub.

19. The heater unit of claim 18, each of the mount fingers including a tab adapted to snap into a respective aperture.

20. The heater unit of claim 14, the hot plate being of nickel-plated aluminum.

21. The heater unit of claim 14, the hub being of polyphenyl sulfone.

22. The heater unit of claim 14, the thin disc of the hot plate being slightly convex.

23. The heater unit of claim 14, the housing having a support, the hub including a plurality of spaced posts coupled to the support.

24. The heater unit of claim 23 further comprising a plurality of threaded inserts each coupling respective ones of the posts to the support.

25. The heater unit of claim 23, the support including a plurality of receptacles, each post defining a tab adapted to snap into respective ones of the receptacles whereby to couple the posts to the support.

26. The heater unit of claim 23 further comprising a plurality of springs associated with the plurality of posts.

27. The heater unit of claim 14, the hub support platform defining a recess, the housing defining an interior chamber, the support platform including an aperture communicating with the recess and the housing interior chamber whereby to define a route for wires between the hot plate and the interior chamber.

28. The heater unit of claim 14, the hub including a support platform defining a recess, the heater unit further comprising a pad in the recess.

29. The heater unit of claim 14, the hub being resiliently mounted to the housing.

* * * * *